US008827335B2

(12) United States Patent
Tortelli et al.

(10) Patent No.: US 8,827,335 B2
(45) Date of Patent: Sep. 9, 2014

(54) MAGNETIC MEDICAL PICKUP DEVICE

(71) Applicants: James Tortelli, Des Moines, IA (US); Michelle A. Tortelli, Hartford, WI (US)

(72) Inventors: James Tortelli, Des Moines, IA (US); Michelle A. Tortelli, Hartford, WI (US)

( * ) Notice: Subject to any disclaimer, the term of this patent is extended or adjusted under 35 U.S.C. 154(b) by 0 days.

(21) Appl. No.: 13/663,611

(22) Filed: Oct. 30, 2012

(65) Prior Publication Data

US 2013/0180875 A1 Jul. 18, 2013

Related U.S. Application Data

(60) Provisional application No. 61/586,873, filed on Jan. 16, 2012.

(51) Int. Cl.
*B65D 85/00* (2006.01)

(52) U.S. Cl.
USPC ............... 294/2; 294/65.5; 294/212; 206/818

(58) Field of Classification Search
USPC ............... 294/65.5, 190, 212, 2, 24; 206/570, 206/571, 350, 776, 818; 220/377
See application file for complete search history.

(56) References Cited

U.S. PATENT DOCUMENTS

| | | | | | |
|---|---|---|---|---|---|
| 2,405,655 | A * | 8/1946 | Kehoe | 294/65.5 |
| 2,848,006 | A * | 8/1958 | Simpson | 134/133 |
| 3,921,983 | A * | 11/1975 | Taylor | 273/148 R |
| 4,046,383 | A * | 9/1977 | Vidnovic | 273/148 R |
| 4,653,789 | A * | 3/1987 | McWilliams et al. | 294/212 |
| 4,802,702 | A * | 2/1989 | Bownds | 294/65.5 |
| 4,886,165 | A * | 12/1989 | Annett | 206/370 |
| 5,181,609 | A * | 1/1993 | Spielmann et al. | 206/370 |
| 5,273,329 | A * | 12/1993 | Wessel | 294/61 |
| 6,273,293 | B1 * | 8/2001 | Carlson | 221/37 |
| 6,325,433 | B1 * | 12/2001 | Nicholson et al. | 294/65.5 |
| 6,669,024 | B2 * | 12/2003 | Ottens | 209/215 |
| 2003/0150860 | A1 * | 8/2003 | Lee | 220/212.5 |

* cited by examiner

*Primary Examiner* — Dean Kramer

(57) ABSTRACT

A magnetic medical pick up device having a top piece and a bottom piece which removeably engage one another with a cavity positioned between the top and bottom piece. At least one magnetic piece is positioned within the cavity and a handle is connected to the top exterior portion of top piece for handling the magnetic medical pick up device. In use, the top piece and bottom piece are separated from one another, and the top piece is positioned over a contaminated medical device. In this position the magnetic attraction of the magnet pulls the contaminated medical device within the cavity and the bottom piece is engaged with the top piece thereby quarantining the contaminated medical device. As at least a portion of the top piece and/or bottom piece are transparent, the contaminated medical device can be inventoried at the end of the procedure while remaining quarantined within the cavity.

1 Claim, 4 Drawing Sheets

18 100 107 29 104 20 106 102 107 40 24 108 28 26

MAGNETIC MEDICAL PICKUP DEVICE

CROSS REFERENCE TO RELATED APPLICATION

This application claims the benefit of U.S. Provisional Application No. 61/586,873 filed Jan. 16, 2012.

BACKGROUND OF THE INVENTION

This invention is directed towards medical devices. More specifically and without limitation, this invention is directed towards medical devices used to pick up other devices.

Current operating procedures require a mandatory count of all items placed on the sterile table for use in invasive surgical operations both before and after surgery. Occasionally items fall to the operating room floor during surgery. This requires a person to manually pick up the dropped item off the floor and quarantine the item. Should the dropped item be a sharp, it still must be picked up, and it must be saved for end of procedure counting and then properly disposed of. This process presents a hazard to the surgical staff as the sharp could potentially puncture or cut the individual during handling. If, however, the dropped item is not picked up it presents a hazard as operating room staff could slip on the item or cut or puncture themselves on the item. Also, if the dropped item is contaminated and it is not immediately picked up, the item could spread contamination in the operating room which must remain as sterile as possible.

In addition to dropping items, surgical devices can also become contaminated by other means. Similarly, these contaminated devices must be quarantined, and saved for end of procedure counting.

One solution developed to retrieve dropped items in an operating room is known as the GOLDEN RETRIEVER™ distributed by Purple Surgical, Cory Bros, and Advanced Medical Innovations. The Golden Retriever™ is a magnetic rod with wheels on each end. A handle is connected to the magnetic rod. When the Golden Retriever™ is rolled over the area where a medical device is dropped, the magnetic rod attracts the metal in the medical device. While the Golden Retriever™ works to pick up devices from the floor, it presents additional problems. Namely, once a contaminated item is picked up by the Golden Retriever™, the Golden Retriever™ itself is contaminated. In addition, a new dangerous condition has developed as the contaminated medical device is now magnetically attached to the rod of the Golden Retriever™ Further, the Golden Retriever™ does nothing to quarantine the contaminated medical device to prevent further contamination.

Therefore, despite these advances, problems still remain. In particular problems remain regarding safely picking up and disposing of dropped contaminated items in operating rooms. Further, problems remain regarding quarantining contaminated items in operating rooms. Still further, problems remain picking up sharps from operating room floors.

Thus it is a primary object of the present invention to provide an apparatus and method for safely picking up dropped items in operating rooms.

Another object of the present invention is to provide an apparatus and method for quarantining contaminated objects in operating rooms.

Yet another object of the present invention is to provide an apparatus and method for safely removing contaminated items from the surgical field while saving them for end of procedure counting.

These and other objects, features, or advantages of the present invention will become apparent from the specification, drawings and claims.

BRIEF SUMMARY OF THE INVENTION

A magnetic medical pick up device having a top piece and a bottom piece which removeably and replaceably engage one another with a cavity positioned between the top piece and the bottom piece. At least one magnetic piece or strip is positioned within the cavity and a handle is connected to the top exterior portion of top piece for handling the magnetic medical pick up device. In use, the top piece and bottom piece are separated from one another, and the top piece is positioned over a contaminated medical device. In this position the magnetic attraction of the magnet pulls the contaminated medical device within the cavity and the bottom piece is engaged with the top piece thereby quarantining the contaminated medical device. As at least a portion of the top piece and/or bottom piece are transparent, the contaminated medical device can be inventoried at the end of the procedure while remaining quarantined within the cavity.

DETAILED DESCRIPTION OF THE PREFERRED EMBODIMENT

With reference to the drawings, a magnetic medical pickup device 10 is presented. Device 10 has a top piece 12 with a flat upper wall 14 that transitions downwardly at its exterior edges to a sidewall 16 that extends perpendicular to upper wall 14 a length past the bottom surface of upper wall 14.

Figure 1:
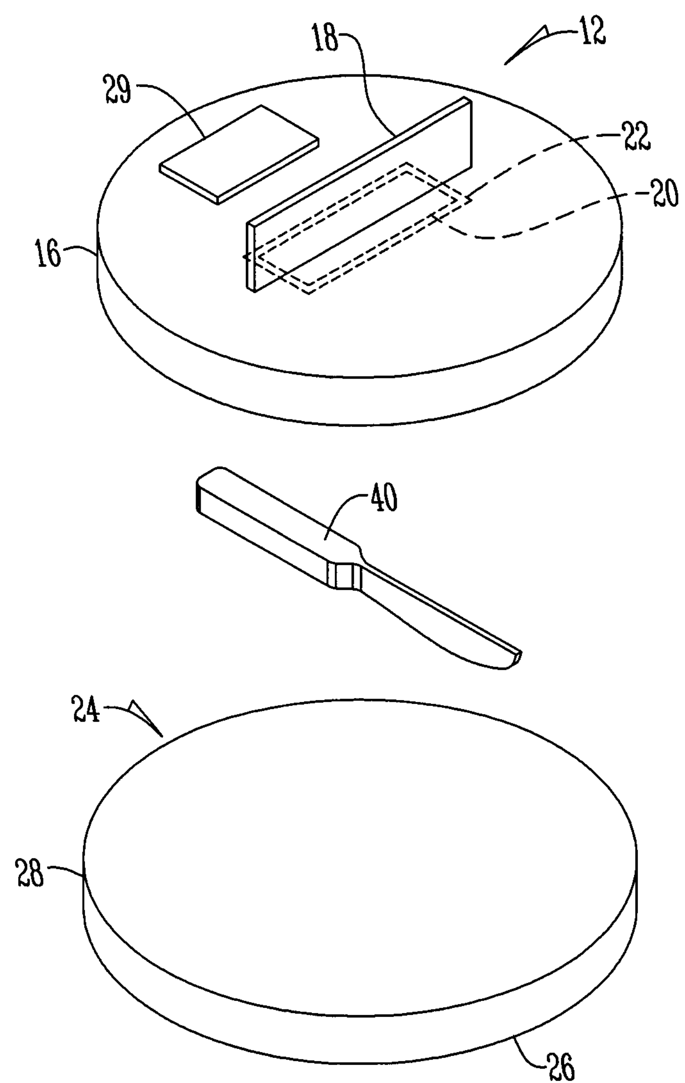
FIG. 1 is a perspective view of a magnetic medical pickup device.
Figure 2:
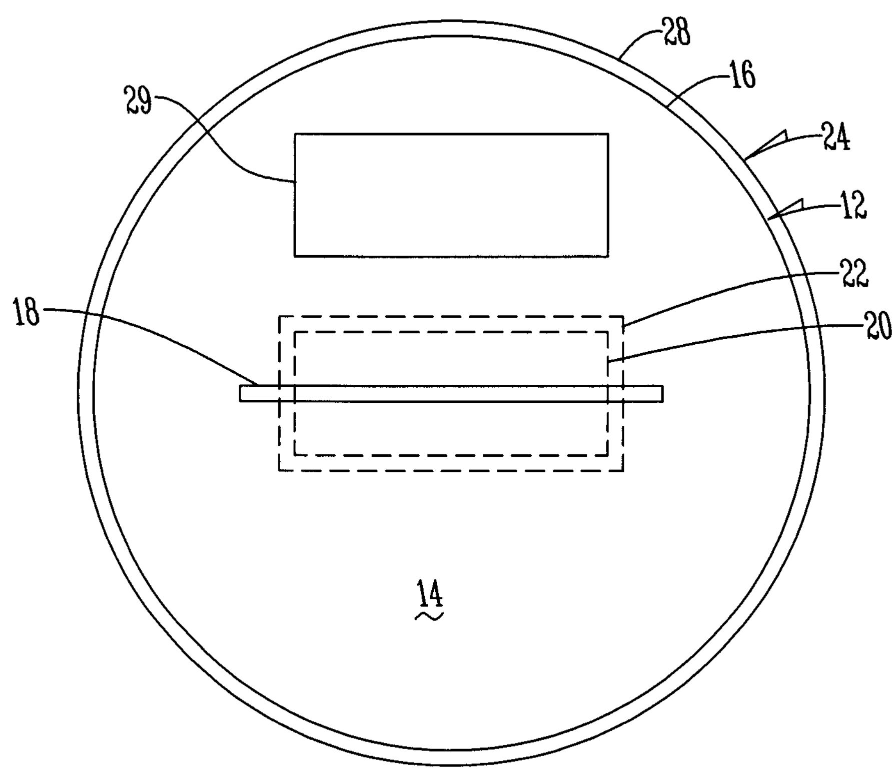
FIG. 2 is a top plan view of a magnetic medical pickup device.
Figure 3:
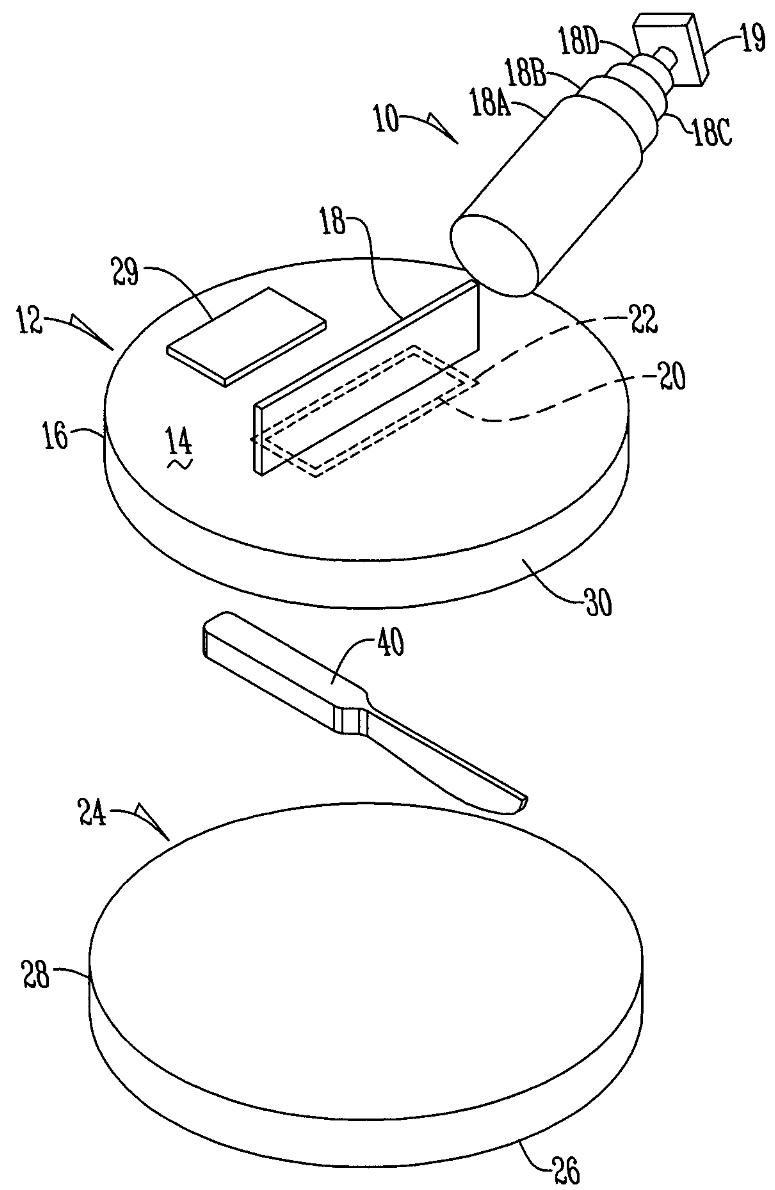
FIG. 3 is a perspective view of a magnetic medical pickup device having an extendible handle.
Figure 4:
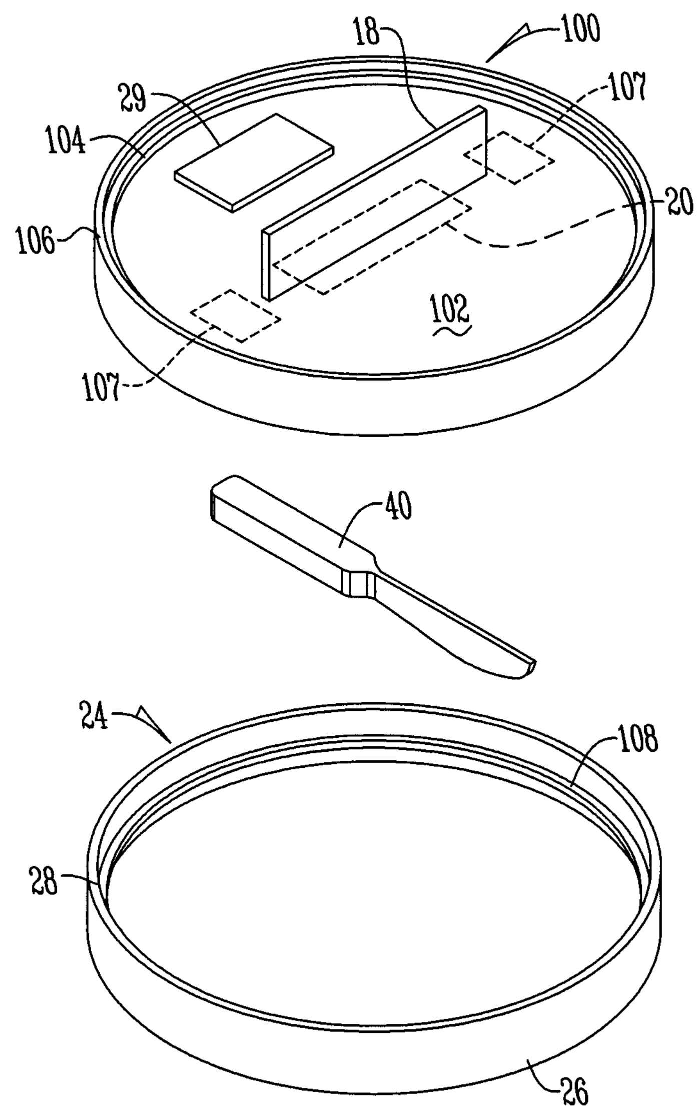
FIG. 4 is a perspective view of a magnetic medical pickup device.

A handle 18 is connected to the top surface of upper wall 14 and extends upwardly therefrom. Handle 18 is of any size and shape, however, preferably, handle 18 only extends across a portion of upper wall 14 and therefore it is narrower in width than top piece 12. Also, the exterior surface of handle 18 preferably has texturing or groves or a coating such as a rubber or the like which improves the ability to grip device 10 while remaining sterile in nature. In one arrangement, as is shown in FIGS. 1-2, handle 18 is rectangularity shaped flange which extends upwardly from the top surface of upper wall 14 only a short length less than the width of the device 10. This arrangement is convenient and useful for using in close proximity to the user. In another arrangement, as is shown in FIG. 3, handle 18 is a telescoping handle that can extend to a long length, many times longer than the width of device 10. This arrangement is convenient and useful for using in distant proximity to the user, such as picking items off of the operating room floor without having to bend over. Although a telescoping handle is shown which can extend, a permanently extended handle is also hereby contemplated. Telescoping handle 18 can extend and retract by any means known in the art such as a plurality of members 18A, 18B, 18C, 18D which meshingly engage one another and extend and retract within one another. Any other extensible member can be used such as folding members, rotating or threaded members, or the like.

Positioned at the end of extendible handle, adjacent the end of segment 18D is a cross member 19 which assists with gripping the end of handle 18 when extended.

Handle 18 is removably and replaceably connected to the top surface of upper wall 14 by any means known in the art such as magnetic attraction, Velcro, gluing, welding, screwing, bolting, snap fitting, integrally molding, or the like. Alternatively, Handle 18 is permanently connected to upper wall 14 by forming the handle 18 within upper wall 14 itself.

A magnetic strip 20 is connected to the bottom surface of upper wall 14. In one arrangement, the bottom surface of upper wall 14 is flat and flush. In this arrangement magnetic strip 20 is flushly connected to the bottom surface of upper wall 14. In another arrangement, a recess 22 is positioned within the bottom surface of upper wall 14. In this arrangement, magnetic strip 20 is positioned within recess 22. In this arrangement, magnetic strip 20 is the same height as is the depth of recess 22 such that when magnetic strip 20 is positioned within recess 22 the bottom surface of upper wall 14 is aligned with the bottom surface of magnetic strip 20 thereby presenting an entirely flat and flush bottom surface of upper wall 14. Magnetic strip 20 is removably and replaceably connected to the bottom surface of upper wall 14 by any means known in the art such as magnetic attraction, Velcro, gluing, welding, screwing, bolting, snap fitting, integrally molding, or the like. Alternatively, magnetic strip 20 is permanently connected to upper wall 14 by forming the magnetic strip 20 within upper wall 14 or magnetizing upper wall 14 itself.

Magnetic medical pickup device 10 also has a bottom piece 24. Bottom piece 24 has a flat bottom wall 26 that transitions upwardly at its exterior edges to a sidewall 28 that extends perpendicular to bottom wall 26 a length past the upper surface of bottom wall 26. Sidewall 28 extends upward above the upper surface of bottom wall 26.

As is shown in FIGS. 1, 2 and 3, top piece 12 and bottom piece 24 are sized and shaped to matingly receive one another in frictional overlapping condition. This mating frictional overlapping condition includes, sizing top piece 12 and bottom piece 24 such that when pressed together sidewall 16 of top piece 12 frictionally overlaps with sidewall 28 of bottom piece 24 to hold the two components together. This mating condition also includes other connecting methods and systems such as a deformable or collapsible lip which when pressed together lockingly engages the two components 12, 24; threads which are added to components 12, 24 to threadably engage one another, alternatively a snap fit arrangement or detent arrangement is used, or any other means of removably and replaceably engaging two components which are known in the art. Alternatively or in addition, the two components 12, 24 are magnetically connected to one another, or to assist with holding the two components 12, 24 together. As is shown in FIGS. 1, 2 and 3, when top piece 12 and bottom piece 24 are engaged with one another a cavity 30 is positioned between the bottom surface of upper wall 14 and the top surface of bottom wall 26, and between the interior most edges of sidewall 16 of top piece 12 and sidewall 28 of bottom piece 24. Preferably, when top piece 12 and bottom piece 24 are engaged with one another they are hermetically sealed thereby preventing any additional contamination from the objects positioned within cavity 30

Top piece 12 and bottom piece 24 are any size and shape to fit and conveniently pick up commonly dropped or contaminated medical devices. As is shown in FIGS. 1-3, top piece 12 and bottom piece 24 are circularly shaped when viewed from the top or bottom. Alternatively, top piece 12 and bottom piece 24 are any other shape such as square, rectangular, oval or the like when viewed from the top or the bottom so as to fit different shaped objects. In addition, the vertical height of cavity 30 is sized to fit the height or width of commonly dropped or contaminated medical devices.

Top piece 12 and or bottom piece 24 are made of any material which is rugged enough for its intended purpose. However, preferably top piece 12 and/or bottom piece 24 are made of a transparent or see through material such that the devices within cavity 30 can be easily counted during end of procedure inventory without breaking the seal of device 10 and further contaminating the environment or exposing those in the room to additional dangers of contaminated sharps. Alternatively, only a portion of either top piece 12 or bottom piece 24 are made of a transparent or see through material, such as a small window 29 placed in the top piece 12 or bottom piece 24.

Device 10 is either reusable or disposable depending on the materials from which it is manufactured. For a reusable device, the device is primarily constructed of metal and glass or ceramic. For a disposable device, the device is primarily made of polymers or plastic or the like. For transparent materials, acrylic, glass, plastic, Plexiglas, or the like are acceptable.

In an alternative arrangement, which is similar to the above-described arrangement, with the following modifications, top piece 100 has a flat upper wall 102 which extends outwardly before terminating at an edge 104. At this exterior edge 104, flat upper wall 102 transitions or arcuately curves upwardly to a sidewall 106 which extends perpendicularly to flat upper wall 102. Top piece 100 fits within and is received by bottom piece 24 as is described above. To ensure that there is adequate space between the bottom surface of top piece 100 and the top surface of bottom piece 24, a stop 108 is positioned on the interior edge of sidewall 28 of bottom piece 24. When the edge of top piece 100 engages stop 108, top piece 100 can go no further within bottom piece 24 thereby providing an adequate amount of space for medical instrument 40.

This arrangement, allows for a medical device 40 to be picked up without a downwardly extending sidewall 16 obstructing the magnet 20 from engaging and holding the medical device 40. That is, this arrangement allows the user to directly engage the medical device 40 by having the magnet being flush with, or extending just out of, the bottom surface of the flat upper wall 102. Alternatively, in this arrangement, as the user can directly engage the medical device 40 with the bottom side of the top piece 100 an adhesive 107 is used which replaces or is used in conjunction with magnet 20. The adhesive 107 is attached in the manner described above with respect to magnet 20, that is adhesively, within a recess, flushly on the bottom surface of top piece 100 or the like. The term "adhesive" is used to describe any device, substance or object capable of bonding to, attracting, holding or sticking to medical device 40 in any way other than or in addition to, magnetic attraction. Adhesives include tape, double sided tape, double sided foam tape, glue, paste, gel, deformable gel, putty, foam, sticky foam, or any other sticky, tacky or deformable object or matter that is capable of attaching to and/or holding medical device 40. In the arrangement where adhesive 107 is used in place or in addition to magnet 20, stop 108 prevents the adhesive 107 from engaging the top surface of bottom piece 24 and thereby prevents the device from being unintentionally used or engaged with the bottom piece 24. Additionally, a cover is placed over the adhesive 20, such as a protective layer of plastic or the like over a piece of double-sided foam tape, which protects the adhesive from being used inadvertently. The protective layer is removed by the user just prior to use.

Also, with the sidewall 106 extending upwardly from the flat upper wall 102, this provides a slight amount of protection for the user, so that they do not accidently contact the medical device 40. Also, with the exterior edge 104 of the flat upper piece 102 arcuately curving upwardly, this allows for easier insertion of the top piece 100 into the bottom piece 28.

In operation, when a medical device 40 is dropped or contaminated in the operating room magnetic medical pickup device 10 is selected to pick up the medical device 40 and quarantine the medical device 40 until the end of procedure inventory. If the contaminated medical device 40 is within close proximity, or arms reach of the user, the user selects the embodiment shown in FIGS. 1-2 by handle 18. If the contaminated medical device is on the floor or out of easy arms reach, the user selects the embodiment having a long or extendable handle, as is shown in FIG. 3. The user also selects the properly sized magnetic medical pickup device 10 to fit the contaminated medical device 40.

Once the proper tool is selected, the user places the open cavity of top piece 12 over the medical device 40. When the magnetic strip 20 comes in close proximity to medical device 40, the magnetic attraction pulls medical device 40 within cavity 30 of the top piece 12 and into frictional locking engagement with magnetic strip 20 and holds the medical device 40 within cavity 30. Once in place, the user places the open end of bottom piece 24 adjacent the open end of top piece 12 and engages the bottom piece 24 and top piece 12 by the means in which they are connected such as frictional engagement, threadably meshing engagement, snap fit, magnetic attraction, or the like. Once top piece 12 and bottom piece 24 are engaged with one another medical device 40 is sealed within cavity 30 no additional contamination or danger can occur from medical device 40. At this point, the magnetic medical pickup device 10 with quarantined medical device 40 is placed aside until end of procedure inventory. During the end of procedure inventory, the medical device 40 can be accounted for by looking through the transparent portions of the device 10 such as clear top piece 12, clear bottom piece 24 or window 29.

From the above discussion it will be appreciated that the magnetic medical pickup device offers many advantages over the prior art. The magnetic medical pickup device described provides an apparatus and method for safely picking up dropped items in operating rooms. The magnetic medical pickup device described provides an apparatus and method for quarantining contaminated objects in operating rooms. The magnetic medical pickup device described provides an apparatus and method for safely removing contaminated items from the surgical field while saving them for end of procedure counting. The magnetic medical pickup device described improves the safety and cleanliness of operating rooms.

It will be appreciated by those of skill in the art that other various modifications could be made to the device without parting from the spirit and scope of the invention. All such modifications and changes fall within the scope of the claims and are intended to be covered thereby.

What is claimed is:

1. A medical pick-up device, comprising: a top piece having a flat upper wall that terminates into an upwardly extending sidewall;

a handle and a magnet connected to the top piece, a bottom piece that is matingly connected to the top piece to form a cavity; and an adhesive is positioned adjacent a bottom surface of the top piece.

* * * * *